US00PP24235P2

(12) United States Plant Patent
Hanes

(10) Patent No.: US PP24,235 P2
(45) Date of Patent: Feb. 11, 2014

(54) *VERBENA* PLANT NAMED 'VEAZ0014'

(50) Latin Name: *Verbena hybrida*
Varietal Denomination: VEAZ0014

(75) Inventor: Mitchell Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 58 days.

(21) Appl. No.: 13/507,804

(22) Filed: Jul. 30, 2012

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — Annette Para
(74) *Attorney, Agent, or Firm* — Joshua L. Price

(57) ABSTRACT

A new *Verbena* plant named 'VEAZ0014' particularly distinguished by the large bold red-purple colored inflorescences, is early to bloom, has great garden performance with exceptional powdery mildew tolerance with semi-upright plant habit.

1 Drawing Sheet

Latin name of the genus and species of the plant claimed: *Verbena hybrida.*

Varietal denomination: 'VEAZ0014'.

BACKGROUND OF THE NEW PLANT

The present invention comprises a new *Verbena*, botanically known as *Verbena hybrida*, and hereinafter referred to by the variety name 'VEAZ0014'.

'VEAZ0014' is a product of a planned breeding program. The new cultivar has large bold red-purple colored inflorescences, is early to bloom, has great garden performance with exceptional powdery mildew tolerance with semi-upright plant habit.

'VEAZ0014' originated from a hybridization made in August 2007 in a greenhouse in Gilroy, Calif. The female parent was the proprietary, unpatented plant designated '05-1892-1' with smaller red flowers when compared to 'VEAZ0014'.

The male parent of 'VEAZ0014' was an unpatented, proprietary plant identified as '07-1985-1' with purple semi-double flowers. The resultant seed was sown in February 2008.

'VEAZ0014' was selected as one flowering plant within the progeny of the stated cross in May 2008 in a greenhouse in Gilroy, Calif.

The first act of asexual reproduction of 'VEAZ0014' was accomplished when vegetative cuttings were propagated from the initial selection in May 2008 in a greenhouse in Gilroy, Calif.

BRIEF SUMMARY OF INVENTION

Horticultural examination of plants grown from cuttings of the plant initiated in May 2008, and continuing thereafter, has demonstrated that the combination of characteristics as herein disclosed for 'VEAZ0014' are firmly fixed and are retained through successive generations of asexual reproduction.

'VEAZ0014' has not been observed under all possible environmental conditions. The phenotype may vary significantly with variations in environment such as temperature, light intensity, and day length.

Plant Breeder's Rights for this cultivar were applied for in Canada on Nov. 1, 2011, No. 11-7418 and at the Community Plant Variety Office on Oct. 28, 2011, No. 2011/2557. 'VEAZ0014' has not been made publicly available more than one year prior to the filing of this application.

The following traits have been repeatedly observed and are determined to be basic characteristics of the new variety. The combination of these characteristics distinguishes this Verbena as a new and distinct variety.

BRIEF DESCRIPTION OF THE PHOTOGRAPHS

The accompanying photographic drawing shows typical inflorescence, foliage and plant characteristics of 'VEAZ0014' with colors being as true as possible with an illustration of this type. The photographic drawing shows a flowering plant of the new variety and a close-up of the inflorescence.

DETAILED BOTANICAL DESCRIPTION

The plant descriptions and measurements were taken in Enkhuizen, The Netherlands in June 2012 under natural light. The plants used were grown in an outdoor window box trial and were approximately 14 weeks old.

The aforementioned photographs were taken in Enkhuizen, The Netherlands in April 2011 in a greenhouse. These plants were approximately 10 weeks of age grown in a greenhouse trial.

Color references are made to The Royal Horticultural Society Colour Chart (R.H.S.) 2001.

TABLE 1

DIFFERENCES BETWEEN THE NEW VARIETY 'VEAZ0014' AND A MOST SIMILAR VARIETY

| | 'VEAZ0014' | 'Sunmaricomu' (Unpatented) |
|---|---|---|
| Flower size: | Larger | Smaller |
| Floret white eye pattern: | No | Yes |

Plant:

*Form, growth and habit.*—Initially mounding, then outwardly spreading and semi-upright vigorous growth habit.

*Plant height.*—15.0 cm.

*Plant height (inflorescence included).*—20.0 cm.

*Plant width.*—50.0 cm.

Roots:

*Number of days to initiate roots and produce roots.*—10-14 days at about 22 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 146A.

*Lower surface.*—RHS 138B.

*Mature, leaf color, upper surface.*—RHS 137B.

*Lower surface.*—RHS 138B.

*Length.*—3.5 cm.

*Width.*—2.5 cm.

*Shape.*—Pinnatifid.

*Base shape.*—Truncate.

*Apex shape.*—Obtuse.

*Margin.*—Dentate with rounded apex.

*Texture, upper surface.*—Hirsute; pilose.

*Lower surface.*—Hirsute; pilose.

*Color of veins, upper surface.*—RHS 137A basally, otherwise indistinct.

*Color of veins, lower surface.*—RHS 141D basally, otherwise indistinct.

*Pattern of veining.*—Pinnate.

*Petioles color.*—RHS 141D.

*Petioles length.*—0.3 cm.

*Petiole width.*—0.25 cm.

*Texture.*—Hirsute.

Stem:

*Quantity of main branches per plant.*—4.

*Color of stem.*—RHS 144A with anthocyanins of about RHS 187A in longitudinal stripes.

*Stem length.*—About 14.0 cm.

*Stem width.*—0.4 cm.

*Stem length of internodes.*—3-3.5 cm.

*Texture.*—Canescent hairs.

*Color of peduncle.*—RHS 144A with anthocyanins of about RHS 187A in longitudinal stripes.

*Length of peduncle.*—About 7.0 cm.

*Peduncle diameter.*—0.3 cm.

*Texture.*—Canescent hairs.

Inflorescence:

*Type.*—Terminal Raceme.

*Blooming habit.*—Flowers continuously.

*Lastingness of individual blooms on the plant.*—About 6-7 days in the greenhouse.

*Fragrance.*—Slight.

*Number of inflorescences per plant.*—About 20 at various stages.

*Horizontal diameter of inflorescence.*—About 6.5 cm.

*Depth of inflorescence.*—About 7.0 cm.

*Number of florets per inflorescence (including any buds at the time).*—Average 32.

Bud (just when opening/showing color):

*Color.*—RHS 71A.

*Length.*—4.4 cm.

*Width.*—0.5 cm.

*Shape.*—Oblong.

Corolla:

*Form.*—Sessile; salverform, composed of 5 petals.

*Immature color, upper surface.*—Closest to RHS 67A but a deeper hue.

*Lower surface.*—RHS 71C.

*Mature color, upper surface.*—Closest to RHS N74A but deeper more purple hue.

*Lower surface.*—RHS 71C.

*Floret diameter.*—2.1 cm.

*Floret length.*—1.8 cm.

*Petal length.*—1.8 cm.

*Petal width.*—1.1 cm.

*Shape.*—Ovate.

*Apex shape.*—Rounded.

*Margin.*—Entire.

*Petal texture, upper surface.*—Papillose.

*Lower surface.*—Papillose.

*Corolla tube length.*—2.0 cm.

*Width.*—0.2 cm.

*Corolla tube color inside.*—RHS 157B.

*Color outside.*—RHS 157A.

*Corolla texture, inside.*—Papillose.

*Outside.*—Puberulous.

*Throat hair color.*—Closest to RHS N155D but whiter.

Calyx:

*Type.*—Five sepals whose margins are fused to each other along their length, with a transparent membrane of less than 0.1 cm in width and with one smaller sepal attached to the base of the calyx.

*Color of sepals.*—RHS 137C.

*Length of sepals.*—1.5 cm.

*Width of sepals.*—0.2 cm.

*Sepal shape.*—Linear.

*Apex shape.*—Apiculate.

*Margins.*—Entire.

*Texture.*—Pubescent.

Reproductive organs:

*Gynoecium.*—Pistil: 1. Pistil length: 1.6 cm. Style color: RHS 145B to RHS 145C. Style length: 1.5 cm. Stigma color: RHS 143B. Ovary color: RHS 144B. Ovary length: 0.1 cm. Ovary width: 0.1 cm.

*Androecium.*—Stamens: Anthers and filaments fused to upper half of corolla tube; four anthers with two pollen sacs per anther. Color of filaments: RHS 145A. Filament length: 0.2 cm. Anther color: RHS N144A. Anther length: 0.15 cm. Color of pollen: RHS 1A. Pollen amount: Very little. Fertility/seed set: Has not been determined to date. Disease/pest resistance: Has not been determined to date.

What is claimed is:

1. A new and distinct variety of *Verbena* plant named 'VEAZ0014' substantially as illustrated and described herein.

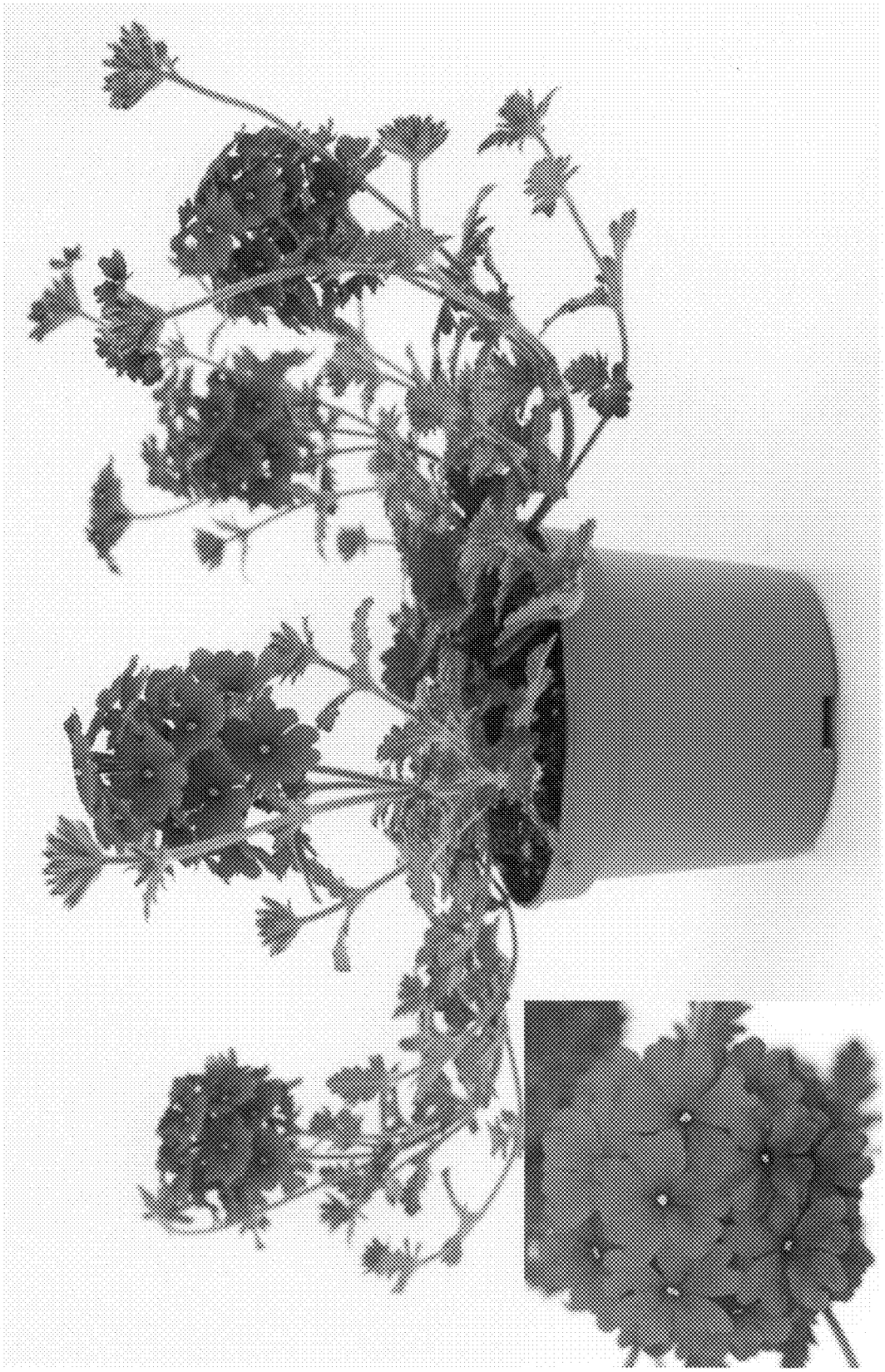

* * * * *